United States Patent [19]
Jan et al.

[11] Patent Number: 5,600,041
[45] Date of Patent: Feb. 4, 1997

[54] PROCESS FOR THE SELECTIVE REMOVAL OF ORGANIC NITRATES FROM A HALOGENATED ORGANIC STREAM CONTAINING TRACE QUANTITIES OF ORGANIC NITRATES

[75] Inventors: Chwu-Ching Jan, Elk Grove Village; Tom N. Kalnes, La Grange; George R. Hibel, Schaumburg, all of Ill.

[73] Assignee: UOP, Des Plaines, Ill.

[21] Appl. No.: 388,112

[22] Filed: Feb. 13, 1995

Related U.S. Application Data

[63] Continuation-in-part of Ser. No. 192,532, Feb. 7, 1994, abandoned, which is a continuation-in-part of Ser. No. 981,962, Nov. 25, 1992, abandoned.

[51] Int. Cl.$^6$ .................................................. C07C 17/38
[52] U.S. Cl. .................. 570/180; 570/177; 570/211; 570/213; 570/238; 570/239; 570/262; 570/263
[58] Field of Search .................................. 570/177, 178, 570/179, 180, 211, 213, 238, 239, 262, 263

[56] References Cited

U.S. PATENT DOCUMENTS

| | | |
|---|---|---|
| 4,895,995 | 1/1990 | James et al. . |
| 5,013,424 | 5/1991 | James, Jr. et al. ................. 208/78 |

*Primary Examiner*—Alan Siegel
*Attorney, Agent, or Firm*—Thomas K. McBride; John G. Tolomei; John G. Cutts, Jr.

[57] ABSTRACT

A process for treating a stream containing halogenated organic compounds and having trace quantities of organic nitrates to produce a stream comprising halogenated organic compounds free from organic nitrates by the utilization of a hydrogenation zone operated at selective hydrogenation conditions in order to convert the organic nitrates to water-soluble nitrogen compounds while minimizing the production of hydrogen halide compounds. The resulting water-soluble nitrogen compounds are removed by extraction with an aqueous stream.

6 Claims, 1 Drawing Sheet

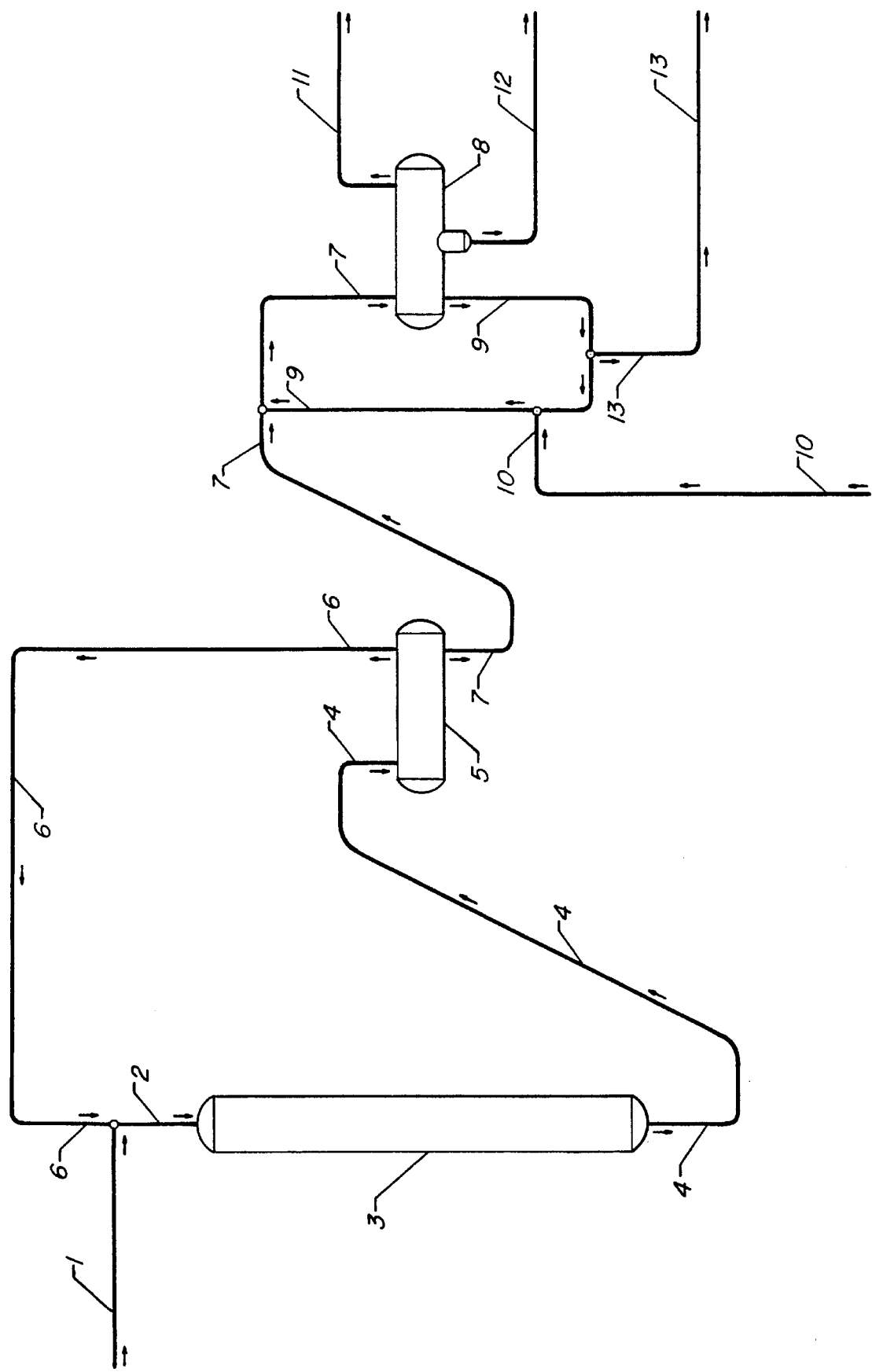

PROCESS FOR THE SELECTIVE REMOVAL OF ORGANIC NITRATES FROM A HALOGENATED ORGANIC STREAM CONTAINING TRACE QUANTITIES OF ORGANIC NITRATES

CROSS-REFERENCE TO RELATED APPLICATION

This is a continuation-in-part of application Ser. No. 08/192,532 filed on Feb. 7, 1994 now abandoned, which is a continuation-in-part of application Ser. No. 07/981,962 filed on Nov. 25, 1992, now abandoned, both of which are incorporated by reference.

FIELD OF THE INVENTION

The field of art to which this invention pertains is the selective removal of organic nitrates from a stream comprising halogenated organic compounds and organic nitrates to produce a stream comprising halogenated organic compounds essentially free from organic nitrates. More specifically, the invention relates to a process for treating a stream containing halogenated organic compounds and having trace quantities of organic nitrates to produce a stream comprising halogenated organic compounds free from organic nitrates by the utilization of a hydrogenation zone operated at selective hydrogenation conditions in order to convert the organic nitrates to water-soluble nitrogen compounds while minimizing the hydrodehalogenation of the halogenated organic compounds.

BACKGROUND OF THE INVENTION

In U.S. Pat. No. 5,013,424 (James, Jr. et al), a process is disclosed wherein a feedstock comprising halogenated organic compounds is contacted with hydrogen in a hydrogenation reaction zone to produce hydrocarbonaceous compounds and at least one water-soluble inorganic halide compound. The '424 patent contemplates processing a feedstock which is free of contaminating organic nitrates which would complicate the operation of the process to produce at least one water-soluble inorganic halide compound. The main thrust of the '424 patent is to essentially convert all of the halide compounds into water-soluble inorganic halide compounds. In the event that the feed to the '424 patent contains significant quantities of organic nitrates, the resulting hydrogen halide compound which is produced would be contaminated by water-soluble nitrogen compounds and its value would thereby be decreased. In addition, the water-soluble nitrogen compounds would react with the co-produced hydrogen halide to form ammonium chloride which forms deposits in the processing plant when the hydrogenation zone effluent is cooled.

Recent developments in the treatment of halogenated organic compounds has created a demand for technology which is capable of treating a stream containing halogenated organic compounds and organic nitrates to selectively convert the organic nitrates to water-soluble nitrogen compounds while minimizing the production of hydrogen halide compounds. With the increased environmental emphasis for the treatment and recycle of waste streams containing organic compounds, there is an increased need for improved processes to accomplish such treatment and recycle. For example, during the disposal or recycle of potentially harmful hydrocarbonaceous waste streams, an important step in the total solution to the problem is the pretreatment or conditioning of an organic stream which facilitates the ultimate resolution to produce product streams which may subsequently be handled in an environmentally acceptable manner. Therefore, those skilled in the art have sought to find feasible techniques to remove organic nitrate compounds from a stream containing halogenated organic compounds and organic nitrate compounds to produce a stream comprising halogenated organic compounds essentially free from organic nitrates which may then be further treated or processed if desired.

It has recently been discovered that when a feedstock comprising halogenated organic compounds and relatively small quantities of organic nitrate compounds is processed to produce water-soluble inorganic halide compounds, several problems are encountered as a result of the conversion of organic nitrate compounds to ammonia and subsequently ammonium chloride. These problems include the need for higher operating temperatures to maintain inorganic halide production, the undesirable contamination of the inorganic halide compound product stream with nitrogen compounds and the plating out of ammonium chloride on the cooler surfaces of the plant as the reactor effluent is cooled in preparation for subsequent separation and product recovery. In many cases, the recovered inorganic halide compound product stream is recycled to production facilities, such as chlorine production, for example, which require high-purity halide compounds without nitrogen contaminants.

BRIEF SUMMARY OF THE INVENTION

The present invention provides a process to produce a stream comprising halogenated organic compounds and essentially free from organic nitrates from a stream comprising halogenated organic compounds and organic nitrates by means of contacting the feed stream and hydrogen with selective hydrogenation catalyst in a hydrogenation zone at hydrogenation conditions to convert the organic nitrates into water-soluble nitrogen compounds while effectively minimizing the production of hydrogen halide compounds. Important elements of the process are the ability to produce a stream containing halogenated organic compounds essentially free of organic nitrates thereby permitting the subsequent conversion of the nitrogen-free stream in a facile manner if desired and conversion of the organic nitrates into water-soluble nitrogen compounds which can be readily separated and recovered for further use or disposal as desired. In accordance with the present invention, "essentially free of organic nitrates" means preferably containing less than about 20 ppm nitrogen and more preferably less than about 10 ppm nitrogen. The present invention enjoys the advantage of selectively purifying a stream containing halogenated organic compounds in a convenient and economical manner. The results of this advantage include the maximum recovery of hydrogen halide in subsequent recovery procedures, reduced operating costs, production of higher quality hydrogen chloride and better on-stream efficiency of subsequent processing procedures.

One embodiment of the invention may be characterized as a process for the selective conversion of organic nitrates contained in a stream comprising halogenated organic compounds and the organic nitrates which process comprises: (a) contacting the stream comprising the halogenated organic compounds and the organic nitrates, and hydrogen with a selective hydrogenation catalyst comprising a refractory inorganic oxide and at least one metallic compound having hydrogenation activity in a hydrogenation zone at hydrogenation conditions selected to produce at least one water-soluble nitrogen compound while minimizing the production of hydrogen halide compounds; (b) separating the resulting effluent from the hydrogenation zone to produce a hydrogen-rich gaseous stream and a liquid stream comprising halogenated organic compounds and water-soluble nitrogen compounds; (c) contacting the liquid stream comprising halogenated organic compounds and water-soluble nitrogen compounds with an aqueous scrubbing solution to absorb at least a portion of the water-soluble nitrogen compounds; (d) recovering an aqueous stream comprising water-soluble nitrogen compounds; and (e) recovering a stream comprising halogenated organic compounds having less than about 20 ppm nitrogen.

Other embodiments of the present invention encompass further details such as preferred feedstocks, hydrogenation catalysts, and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved process for the selective conversion and removal of organic nitrates from a stream containing halogenated organic compounds and organic nitrates while minimizing the production of hydrogen halide compounds. A wide variety of organic streams containing halogenated organic compounds and organic nitrates are to be candidates for feed streams in accordance with the process of the present invention. Examples of organic streams which are suitable for treatment by the process of the present invention are halogenated by-products from propylene oxide, epichlorohydrin, acetaldehyde, vinyl chloride monomer, brominated phenol and bisphenol, synthetic refrigerants and other similar chemical production plants as well as spent halogenated solvents and residues derived from the recycle of such solvents. The organic nitrates are preferably present in the feedstock in an amount from about 20 wppm to about 2 weight percent. The halogenated organic compounds are preferably present in the feedstock in an amount from about 1 to about 99 weight percent.

In accordance with the subject invention, a feed stream comprising halogenated organic compounds and organic nitrates is contacted in the presence of hydrogen with a selective hydrogenation catalyst in a hydrogenation zone at hydrogenation conditions selected to produce at least one water-soluble nitrogen compound while minimizing the production of hydrogen halide compounds. The water-soluble nitrogen compound is preferably selected from the group consisting of ammonia, ammonium chloride, primary amines, secondary amines, tertiary amines, and nitriles. The catalytic hydrogenation zone may contain a fixed, ebullated or fluidized catalyst bed. This reaction zone is preferably maintained under an imposed pressure from about atmospheric (0 kPa gauge) to about 2,000 psig (13790 kPa gauge) and more preferably under a pressure from about 100 psig (689.5 kPa gauge) to about 1000 psig (6895 kPa gauge). Suitably, such reaction is conducted with a maximum catalyst bed temperature in the range of about 60° F. (15° C.) to about 212° F. (100° C.) selected to produce at least one water-soluble nitrogen compound while minimizing the production of hydrogen halide compounds. In accordance with the present invention, it is contemplated that the desired hydrogenation conversion includes primarily the selective conversion of water-insoluble organic nitrates. As used herein, the expression "organic nitrates" refers to water-insoluble compounds containing nitrogen. Preferred organic nitrates are selected from the group consisting of methyl nitrate and chloropropyl nitrate. Hydrogen is present in the hydrogenation zone in an amount at least great enough to satisfy the stoichiometric hydrogen required for the selective conversion of organic nitrates. Further preferred operating conditions include liquid hourly space velocities in the range from about 0.05 $hr^{-1}$ to about 20 $hr^{-1}$ and hydrogen circulation rates from about 1 standard cubic feet per barrel (SCFB) (0.17 normal $m^3/m^3$) to about 1000 SCFB (168 normal $m^3/m^3$), preferably from about 10 SCFB (1.68 normal $m^3/m^3$) to about 500 SCFB (84 normal $m^3/m^3$) when hydrogen circulation is used.

The preferred catalytic composite disposed within the hereinabove described hydrogenation zone can be characterized as containing a metallic component having hydrogenation activity, which component is combined with a suitable refractory inorganic oxide carrier material or carbon-based material of either synthetic or natural origin. The precise composition and method of manufacturing the carder material is not considered essential to the present invention. Preferred carrier materials are alumina, silica and mixtures thereof. Suitable metallic components having hydrogenation activity are those selected from the group comprising the metals of Groups VI-B and VIII of the Periodic Table, as set forth in the *Periodic Table of the Elements,* E. H. Sargent and Company, 1964. Thus, the catalytic composites may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VI-B are generally present in an amount within the range of about 1 to about 20 weight percent, the iron-group metals in an amount within the range of about 0.2 to about 10 weight percent, whereas the noble metals of Group VIII are preferably present in an amount within the range of about 0.1 to about 5 weight percent, all of which are calculated as if these components existed within the catalytic composite in the elemental state. In accordance with a preferred embodiment of the present invention, the preferred catalysts contain alumina and palladium. It is further contemplated that hydrogenation catalytic composites may comprise one or more of the following components: cesium, francium, lithium, potassium, rubidium, sodium, copper, gold, silver, cadmium, mercury and zinc.

The resulting effluent from the selective hydrogenation zone is, in one embodiment, preferably admitted to a separation zone which is maintained at essentially the same pressure as the hydrogenation zone wherein a hydrogen-rich gaseous phase is produced and recycled to the hydrogenation zone. A liquid phase is removed from the separation zone and is contacted with an aqueous scrubbing solution and the resulting admixture is introduced into a second separation zone in order to produce a gaseous stream, a halogenated organic stream and a spent aqueous stream. The contact of the effluent from the first separation zone with the aqueous scrubbing solution may be performed in any convenient manner and is preferably conducted by co-current, in-line mixing which may be promoted by inherent turbulence, mixing orifices or any other suitable mixing means. The aqueous scrubbing solution is preferably introduced in an amount from about 0.05 to about 200 vol. % based on the liquid effluent from the first separation zone. The aqueous scrubbing solution is selected depending on the characteristics of the original feedstock. In accordance with the present invention, the feedstock comprises halogenated compounds and the aqueous scrubbing solution preferably contains an acid compound such as hydrogen chloride to absorb the water-soluble nitrogen compounds which are produced in the hydrogenation zone.

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such equipment is well within the purview of one skilled in the art.

With reference now to the drawing, a liquid feed stream comprising halogenated organic compounds and organic nitrates is introduced into the process via conduit 1, joined by a recycle, hydrogen-rich gaseous stream which is provided via conduit 6 and the resulting admixture is introduced into hydrogenation zone 3 via conduit 2. A resulting effluent stream from hydrogenation zone 3 is removed via conduit 4 and introduced into high pressure vapor/liquid separator 5. A hydrogen-rich gaseous stream is removed from high pressure vapor/liquid separator 5 via conduit 6 and is recycled to hydrogenation zone 3 as hereinabove described. Since hydrogen is lost in the process by means of a portion of the hydrogen being dissolved in the exiting liquid stream and hydrogen being consumed during the selective conversion of the organic nitrates, it is necessary to supplement the hydrogen-rich gaseous stream with makeup hydrogen from some suitable external source, for example, a catalytic reforming unit or a hydrogen plant. Makeup hydrogen may be introduced into the system at any convenient and suitable point not shown in the drawing. A liquid stream containing halogenated organic compounds and having a reduced level of organic nitrates is removed from high pressure vapor/liquid separator 5 via conduit 7 and is contacted with an aqueous scrubbing solution which is supplied via conduit 9 and the resulting admixture is introduced via conduit 7 into low pressure vapor/liquid separator 8. A gaseous stream comprising dissolved hydrogen and any other light gaseous compounds present is removed from low pressure vapor/liquid separator 8 via conduit 11 and recovered. A liquid stream containing halogenated organic compounds and having a reduced level of organic nitrates is removed from low pressure vapor/liquid separator 8 via conduit 12 and recovered. An aqueous scrubbing solution is removed from low pressure vapor/liquid separator 8 via conduit 9 and is contacted with the liquid effluent from the high pressure vapor/liquid separator 5 as described hereinabove. Fresh, makeup aqueous scrubbing solution is introduced via conduit 10 into the circulating aqueous scrubbing solution which is transported via conduit 9. Spent aqueous scrubbing solution is removed from low pressure vapor/liquid separator 8 via conduit 9 and conduit 13 and is recovered.

EXAMPLE 1

A feed stream containing chlorinated by-products from a propylene oxide production plant having the characteristics presented in Table 1 was charged at a rate of 100 mass units per hour to a hydrogenation zone containing a hydrogenation catalyst containing alumina and palladium, and operated at conditions including a pressure of 750 psig, a hydrogen circulation rate of 40,000 SCFB and a catalyst peak temperature of about 572° F. (300° C.). The object of this example is to hydrogenate the chlorinated organic compounds to produce hydrocarbons and hydrogen chloride. After the hydrogenation zone was operated for about 35 days, the reactor circuit started to develop increasing pressure drop which indicated partial plugging and the activity of the catalyst was observed to prematurely decline. The plant was subsequently shut down and the hydrogenation zone outlet piping was inspected and found to contain significant deposits of ammonium chloride. Before the plant was shut down, a resulting liquid product was recovered from the effluent of the hydrogenation zone in an amount of about 100 mass units per hour and having the characteristics presented in Table 2.

TABLE 1

| CHLORINATED BY-PRODUCT FEEDSTOCK ANALYSIS | |
|---|---|
| Dichloropropane, weight percent | 90 |
| Epichlorohydrin, weight percent | 1 |
| Dichloropropyl Ether, weight percent | 8.9 |
| Chloropropyl Nitrate, weight percent | ~0.1 |
| Total Nitrogen, weight ppm | ~100 |

TABLE 2

| HYDROGENATION ZONE EFFLUENT ANALYSIS, WEIGHT PERCENT OF FEED | |
|---|---|
| Hydrogen Chloride | 63.9 |
| Propane | 38.7 |
| Other | 0.9 |
| Total | 103.5 |

After the premature plant shutdown was experienced, the feed was inspected and analyzed and it was determined that the feed unexpectedly contained low quantities of organic nitrate compounds which were found to be soluble in the feed and not extractable with common extraction solvents.

EXAMPLE 2

This example was performed in accordance with the present invention. A feed stream containing chlorinated by-products from a propylene oxide production plant having the characteristics presented in Table 1 was charged at a rate of 100 mass units per hour to a hydrogenation zone containing a hydrogenation catalyst containing alumina and palladium, and operated at conditions including a pressure of 200 psig (1379 kPa gauge), a hydrogen to feed ratio of 300 SCFB (84.3) $m^3/m^3$ and a catalyst peak temperature of about 95° F. (35° C.). These operating conditions were selected to convert the organic nitrate compounds to water-soluble nitrogen compounds while minimizing the production of hydrogen halide compounds. These conditions are less severe than those used in Example 1 and were selected in accordance with the present invention.

A resulting liquid product was recovered from the effluent of the hydrogenation zone in an amount of about 100 mass units per hour and was water washed to extract the water-soluble nitrogen compounds. The resulting water washed liquid was found to have the characteristics presented in Table 3.

TABLE 3

| HYDROGENATION ZONE LIQUID EFFLUENT ANALYSIS | |
|---|---|
| Dichloropropane, weight percent | 90 |
| Epichlorohydrin, weight percent | <0.1 |
| Dichloropropyl Ether, weight percent | 9 |
| Chloropropyl Nitrate, weight percent | <0.01 |
| Chlorinated Propanol, weight percent | 0.9 |
| Total Nitrogen, weight ppm | <10 |

EXAMPLE 3

The conversion process described in Example 1 was repeated with the exception that a feed having the characteristics presented in Table 3 was used. A resulting product recovered from the effluent of the hydrogenation zone was essentially the same as shown in Table 2.

The plant was continuously operated for about 60 days without any detectable increased pressure drop and the catalyst stability was observed to be superior to that in Example 1.

The foregoing description, drawing and examples clearly illustrate the advantages encompassed by the process of the present invention and the benefits to be afforded with the use thereof.

What is claimed:

1. A process for the selective conversion of organic nitrates contained in a stream comprising halogenated organic compounds and said organic nitrates which process comprises:

(a) contacting said stream comprising said halogenated organic compounds and said organic nitrates, and hydrogen with a selective hydrogenation catalyst comprising a refractory inorganic oxide and at least one metallic compound having hydrogenation activity and selected from the group consisting of Groups VIB and VIII of the Periodic Table in a hydrogenation zone at hydrogenation conditions including a pressure from about atmospheric to about 2000 psig, a temperature from about 60° F. to about 212° F., a liquid hourly space velocity from about 0.05 hr$^{-1}$ to about 20 hr$^{-1}$ and a hydrogen circulation rate from about one to about 1000 SCFB selected to produce at least one water-soluble nitrogen compound while minimizing the production of hydrogen halide compounds;

(b) separating the resulting effluent from said hydrogenation zone to produce a hydrogen-rich gaseous stream and a liquid stream comprising halogenated organic compounds and water-soluble nitrogen compounds;

(c) contacting said liquid stream comprising halogenated organic compounds and water-soluble nitrogen compounds with an aqueous scrubbing solution to absorb at least a portion of said water-soluble nitrogen compounds;

(d) recovering an aqueous stream comprising water-soluble nitrogen compounds; and (e) recovering a stream comprising halogenated organic compounds having less than about 20 ppm nitrogen.

2. The process of claim 1 wherein said stream comprising halogenated organic compounds and organic nitrates is selected from the group consisting essentially of halogenated by-products from propylene oxide, epichlorohydrin, acetaldehyde, brominated phenol and bisphenol, synthetic refrigerant and vinyl chloride monomer production plants, spent halogenated solvents and residues derived from the recycle of such solvents.

3. The process of claim 1 wherein said hydrogenation catalyst comprises alumina and palladium.

4. The process of claim 1 wherein said organic nitrates are present in said stream comprising halogenated organic compounds in an amount from about 20 wppm to about 2 weight percent.

5. The process of claim 1 wherein said stream comprising halogenated organic compounds contains halogenated organic compounds in an amount from about 1 to about 99 weight percent.

6. The process of claim 1 wherein said aqueous scrubbing solution is introduced in an amount from about 0.05 to about 200 volume percent based upon said liquid stream comprising halogenated organic compounds and water-soluble nitrogen compounds.

* * * * *